United States Patent [19]

Quesenberry

[11] Patent Number: 5,665,350

[45] Date of Patent: Sep. 9, 1997

[54] CELL CYCLE DEPENDENT TRANSPLANTATION AND EX VIVO GENE THERAPY

[75] Inventor: Peter J. Quesenberry, Shrewsburg, Mass.

[73] Assignee: University of Massachusetts Medical Center, Worcester, Mass.

[21] Appl. No.: 344,080

[22] Filed: Nov. 23, 1994

[51] Int. Cl.$^6$ .............................. A61K 48/00; C12N 5/08
[52] U.S. Cl. ........................................ 424/93.21; 424/93.7
[58] Field of Search .............................. 435/240.1, 240.2, 435/240.31, 7.24, 172.3; 530/387.1; 604/305; 514/44, 12, 2; 424/93.21, 93.2

[56] References Cited

U.S. PATENT DOCUMENTS

| | | | |
|---|---|---|---|
| 4,396,601 | 8/1983 | Salser et al. | 424/93.21 |
| 5,032,407 | 7/1991 | Wagner et al. | 424/93.21 |
| 5,061,620 | 10/1991 | Tsukamoto et al. | 435/7.21 |
| 5,437,994 | 8/1995 | Emerson et al. | 435/240.2 |

FOREIGN PATENT DOCUMENTS

| | | |
|---|---|---|
| 2086844 | 1/1993 | Canada . |
| 9411493 | 5/1994 | WIPO . |

OTHER PUBLICATIONS

Marshall, Science, 269, 1995, 1004–1012.
Harrison, Blood, 81 (10), 1993, 2473–2474.
Stewart et al., 81 (10), 1993, 2566–2571.
Kohn, Curr. Opin. Pediatrics, 1995, 7, 56–63.
Gutierrez et al., The Lancet, vol. 339, 1992, 715–721.
Marshall, Science, 269, 1995, 1050–1055.
Miller et al., FASEBJ., 1994, 9, 190–199.
Culver et al., Trends Genetics, 10(5), 1994, 174–178.
Hodgson, Exp. Opin. Ther. Pat., 5(5), 1995, 459–468.
Barlogie, B.,"Hemopoietic stem cell transplant for multiple myeloma (MM)", 1993,Leukemia, 7:1095.
Biron, P. et al., "Autologous Bone Marrow Transplantation: Proceedings of the First International Symposium", Dicke, K.A. et al., eds, pp. 203–210; Massive Chemotherapy and Autologous Bone Marrow Transplantation in Progressive Disease of Nonseminomatous Testicular Cancer:A Phase II Study on 15 patients, 1985.
Breacher, G. et al., "Special proliferative sites are not needed for seeding and proliferation of transfused bone marrow cells in normal syngeneic mice", 1982, PNAS USA 79:5085–5087.
Cheson, B.D. et al., "Autologous bone marrow transplantation. Current status and future directions", 1989, Ann. Intern. Med. 110(1):51–65.
Crittenden, R. et al., "Repetitive Marrow Transplantation:A Model for Autologous Gene Therapy", 1993, Experimental, Hematology, 21:1016, abstract 30.
Peters, S.Q. et al., "Cytokine Incubation of Murine Marrow Cells Impairs Repopulating Capacity in normal (Non–myeloablated) Hosts", 1994, Experimental Hematology, 22(8):823, abstract 547.
Peters, W. P., "The Rationale for High–Dose Chemotherapy with Autologous Bone Marrow Support in Treating Breast Cancer", 1985, AMBT supra, pp. 189–195.
Ramshaw, H.S. et al.,"Effect of cell cycle on the engraftment of murine bone marrow into unmyeloablated hosts", 1994, Experimental Hematology, 22:823, abstract 548.
Saxe, D.F. et al., "Transplantation of Chromosomally Marked Syngeneic Marrow Cells into Mice Not Subjected to Hematopietic Stem Cells Depletion", 1984, Exp. Hematol. 12:277–283.
Stewart et al., "Long–term engraftment of normal and post–5–fluorouracil murine marrow into normal nonmyeloablated mice", 1993, Blood 81(10):2566–2571.
Sullivan, K.M., "Marrow transplantation for disorders of hematopoiesis", 1993, Leukemia, 7:1098–1099.
Takvorian, T, et al., "Prolonged disease–free survival after autologous bone marrow transplantation in patients with non–Hodgkins's lymphoma with a poor prognosis", 1987, N. Engl. J. Med. 316:1499–1505.
Wheeler, C. et al., "Cyclophosphamide, carmustine, and etoposide with autologous bone marrow transplantation in refractory Hodgkin's disease and non–Hodgkin's lymphomna:a dose–finding study", 1990, J. Clin. Oncol. 8(4):648–656.
Yeager, A.M. et al., "Autologous bone marrow transplantation in patients with acute nonlymphocytic leukemia, using ex vivo marrow treatment with 4–hydroperoxycyclophosphamide", 1986, N. Eng. J. Med. 315(3:141–147.

*Primary Examiner*—Jacqueline M. Stone
*Assistant Examiner*—Andrew Milne
*Attorney, Agent, or Firm*—Fish & Richardson P.C.

[57] ABSTRACT

Methods for the enhancement of bone marrow stem cell engraftment are provided for use in transplantation therapy and ex vivo gene therapy of a mammal. The methods involve the transplantation of quiescent stem cells for transplantation therapy and quiescent transfected stem cells for ex vivo gene therapy.

6 Claims, 2 Drawing Sheets

CELL CYCLE DEPENDENT TRANSPLANTATION AND EX VIVO GENE THERAPY

STATEMENT AS TO FEDERALLY SPONSORED RESEARCH

This invention was made at least in part with funds from the Federal government, and the government therefore has rights in the invention.

BACKGROUND OF THE INVENTION

The invention relates to the field of stem cell engraftment and human ex vivo gene therapy.

Bone marrow transplantation is often accompanied by marrow cytotoxic therapy in order to create marrow space or niches. The usual method of creating such niches is by irradiation and/or chemotherapy treatment. This practice has been challenged by Brecher, Saxe and colleagues, who demonstrated that bone marrow cells (e.g., hematopoietic stem cells) engraft into normal non-myeloablated hosts (Brecher, G. et al. (1982) PNAS USA 79:5085; and Saxe, D. F. et al. (1984) Exp. Hematol. 12:277). These investigators showed varying levels of engraftment up to 25% after infusion of normal bone marrow into non-myeloablated hosts.

One theoretical approach to transplantation involves procurement of stem cells for transplantation followed by expansion of the stem cells to increase their number prior to infusion into the host. Cellular expansion and/or induction into active cell cycling is accomplished by contacting cytokines or other agents, such as 5-fluorouracil, with the stem cells in vivo, if expansion occurs prior to collection of stem cells; or in vitro, if expansion occurs following collection of stem cells.

Additionally, cytokines have been used in various combinations to enhance retroviral integration into stem cells by increasing the percent of stem cells in the process of active cell cycle. Subsequent to retroviral integration, these actively cycling transfected stem cells are introduced into a mammal so that they engraft in the bone marrow of the mammal. Thus the success of ex vivo gene therapy is dependent not only on the efficiency of retroviral integration, but also on the efficiency of transfected stem cell engraftment.

There is a great need for methodologies to enhance engraftment of stem cells in a host mammal for the purpose of improved human bone marrow transplantation therapy as well as for improved human ex vivo gene therapy.

SUMMARY OF THE INVENTION

Applicant discloses that rendering cells quiescent prior to transplantation results in improved engraftment. Accordingly, the invention features a method of stem cell transplantation for enhancing engraftment of the transplanted stem cells, wherein the stem cells are expanded to produce a population of expanded stem cells. The expanded stem cells are next treated so that a majority of them become quiescent stem cells, and the quiescent stem cells are then introduced into a mammal by standard stem cell transplantation techniques. In preferred embodiments the mammal is a non-myeloablated host mammal, preferably a human patient.

Stem cells are expanded and/or treated to enter active cell cycling in vivo or in vitro by methods well known to those skilled in the art and include, but are not limited to, the administration of a cytokine (e.g., IL-3-CHO, IL-6, IL-11, and the like) to the stem cell in vivo or in vitro; and administration of 5-fluorouracil (5-FU) in vivo.

Expanded and/or actively cycling stem cells are induced to become quiescent according to the invention by methods well known to those of ordinary skill in the relevant arts and include, but are not limited to, serum starvation and removal of the expanding or cell cycling-inducing agent. Cells are judged to be quiescent when fewer than 30%, preferably fewer than 10%, more preferably fewer than 5% of the cells are judged to be progressing through the cell cycle as determined by the high specificity tritiated thymidine [$^3$HtdR] suicide technique which selects only fully proliferating cells (i.e. replicating cells). Quiescent cells can also be observed by the lack of incorporation of a radio-labelled nucleotide into the DNA of a representative portion of the cell population of interest. Quiescent cells are also observed as exhibiting a single DNA peak as measured by flow-cytometry (a single peak indicates that the cells are quiescent, while more than one peak indicates DNA synthesis).

The invention also features a method of ex vivo gene therapy in which the stem cells are induced to proliferate for retroviral vector integration and then induced to become quiescent prior to introduction into a mammal. In preferred embodiments, the method is used for treating an inherited, an acquired, or a metabolic deficiency in a mammal (such as a human). For example, the transfected stem cells may contain expressible DNA for the production of antisense RNA in order to reduce the expression of an endogenous gene of the mammal. In other preferred embodiments, the transfected stem cell may contain DNA encoding a protein capable of preventing or treating an inherited or acquired disease (e.g., Factor VIII deficiency in hemophilia, cystic fibrosis, and adenosine deaminase deficiency).

Infused cells or their progeny preferably contain a marker such that the infused cells are observable in a population of host cells for the purpose of measuring the level of engraftment.

Another embodiment of the invention is the method of transplanting a predetermined number of quiescent stem cells into a non-myeloablated host mammal in which a first fraction of the stem cells is introduced into the host mammal at a first point in time followed by introducing thereafter the remaining cells in at least 5, and not greater than 15, additional administrations. Preferably each administration is spaced from the other by at least 12 hours. At a final point in time a final fraction of the predetermined number of cells is introduced such that all of the cells have been introduced into the host mammal.

The invention also features a method of ex vivo gene therapy in which transfected pluripotent hematopoietic stem cells are treated to become quiescent transfected stem cells. A predetermined number of the transfected stem cells are introduced into the host mammal such that a first fraction of the cells are introduced at a first point in time followed by introducing thereafter the remaining cells in at least 5, and not greater than 15, additional administrations, each administration being spaced from the other by at least 12 hours. At a final point in time, a final fraction of the predetermined number of transfected quiescent stem cells is introduced such that all of the original predetermined number of cells have been introduced into the host mammal.

In a preferred embodiment of the scheduled transplantation for enhancement of engraftment of quiescent stem cells or quiescent transfected stem cells, the scheduled transplantation involves a predetermined number of cells wherein the number is at least $1 \times 10^8$ cell/kg body weight of the host mammal and not more than $8 \times 10^9$ cell/kg body weight of the host mammal.

In another preferred embodiment of the scheduled transplantation method of enhancing engraftment of quiescent stem cells or transfected stem cells carrying a foreign gene integrated into the chromosonal DNA of the cell, the fractions of the predetermined stem cells are substantially equal in number of cells. Preferably, the introduction of the quiescent stem cells, or quiescent transfected stem cells, preferably occurs at least 5, and not more than 15, days after the first introduction of a fraction of the stem cells. Preferably, the introductions of said cells are spaced approximately equally in time from the first introduction to the final introduction of the cells.

By the term "stem cell" or "hematopoietic stem cell" is meant a pluripotent cell of the hematopoietic system capable of differentiating into cells of the lymphoid and myeloid lineages.

By the term "transfected stem cell" is meant a stem cell into which an exogenous gene has been introduced by retroviral infection or other means well known to those of ordinary skill in the art.

By the term "ex vivo gene therapy" is meant the in vitro transfection or retroviral infection of stem cells to form transfected stem cells prior to introducing the transfected stem cells into a mammal.

By the term "quiescent stem cell" is meant a stem cell in the $G_1$ or $G_0$ phase of the cell cycle. A population of cells is considered herein to be a population of quiescent cells when at least 50%, preferably at least 70%, more preferably at least 80% of the cells are in the $G_1$ or $G_0$ phase of the cell cycle. Quiescent cells exhibit a single DNA peak by flow-cytometry analysis, a standard technique well known to those of ordinary skill in the arts of immunology and cell biology. Another technique useful for determining whether a population of cells is quiescent is the addition of a chemical agent to the cell culture medium that is toxic only to actively cycling cells (i.e., DNA synthesizing cells) and does not kill quiescent cells. Non-exclusive examples of such chemical agents include hydroxyurea and high specific activity tritiated thymidine ($^3$HtdR). A population of cells is evaluated as to the percent in an actively cycling state by the percent of the cell population killed by the chemical agent. A cell population in which in vitro tritiated thymidine killing is less than approximately 30%, preferably less than approximately 10%, more preferably less than approximately 5% are considered to be quiescent.

By the term "substantially equal fractions" or "substantially equal in number of cells" is meant a fraction of a total number of cells whereby the fraction contains the same number of cells as another fraction of the total and whereby each fraction is preferably within 50%, more preferably within 20% of another fraction in number of cells.

Cycling stem cells can be treated to become quiescent by serum or isoleucine starvation. Quiescence can also be induced by reduction of nutrients in the culture medium such that the cycling stem cells enter and remain in the $G_1$ or $G_0$ phase of the cell cycle while the nutrient level is reduced. These methods can be used alone or in combination.

By the term "expanded population" is meant a population of cells, wherein at least 50% of the cells have divided at least once. In certain embodiments of the invention, the cells may be induced to divide by the administration of cell cycling agents such as 5-FU and/or cytokines such as IL-3-CHO, IL-6, IL-11 and other growth stimulating factors well known to those of ordinary skill in the art of immunology.

By the term "non-myeloablated host mammal" is meant a mammal which has not undergone irradiation, or other treatment (such as chemical treatment) well known to those of ordinary skill in the art, to cause the death of at least 50% of the bone marrow cells of the mammal.

The invention provides methods for the treatment of disorders of cells of the myelolymphoid cell lineage. The invention affords unique and critical advantages over previous methods. Specifically, the invention provides for increased engraftment of transplanted cells by transplantation of quiescent stem cells or quiescent transfected stem cells into a host mammal, preferably a non-myeloablated host mammal. Such increased stem cell engraftment is useful in diseases treatable by bone marrow transplantation as well as in diseases treatable by ex vivo gene therapy using transfected hematopoietic stem cells. Such transplantation of quiescent stem cells and the resultant increased engraftment permits amplification of a desired therapeutic effect.

The improved engraftment achieved using the method of the invention may also be useful in high-dose chemotherapy regimens. The hematologic toxicity observed with multiple cycles of high-dose chemotherapy is relieved by conjunctive administration of autologous hematopoietic stem-cells. Diseases for which reinfusion of stem cells (cells not induced to be quiescent) has been described include acute leukemia, Hodgkin's and non-Hodgkin's lymphoma, neuroblastoma, testicular cancer, breast cancer, multiple myeloma, thalassemia, and sickle cell anemia (Cheson B. D., et al. (1989) Ann Intern Med. 110:51–65; Wheeler, C. et al. (1990) J. Clin. Oncol. 8:648–656; Takvorian, T. et al. (1987) N. Engl. J. Med. 316:1499–1505; Yeager, A. M. et al. (1986) N. Eng. J. Med. 315:141–147; Biron, P. et al. (1985) in *Autologous Bone Marrow Transplantation: Proceedings of the First International Symposium*, Dicks, K. A. et al., eds, p. 203; Peters, W. P. (1985) ABMT, supra, p. 189; Barlogie, B. (1993) Leukemia 7:1095; Sullivan, K. M. (1993) Leukemia 7:1098–1099). Treatment of such diseases can be improved by the method of the present invention of administering cells known to be quiescent and therefore capable of engrafting at an increased level.

Another advantage of the invention is the reduced risk to the recipient of the transplanted cells since no myeloablation is necessary to achieve superior short and long-term engraftment in the non-myeloablated host mammal.

Another advantage of the invention is the ability to use bone marrow, mobilized peripheral blood, and cord blood stem cells in clinical transplant therapy or ex vivo gene therapy.

An advantage of the present invention is its ability to provide useful methods for increased engraftment of stem cells or transfected stem cells by controlling the cell cycle state of the transplanted cells.

Other features and advantages of the invention will be apparent from the following description of the preferred embodiments thereof, and from the claims.

BRIEF DESCRIPTION OF THE DRAWINGS

FIG. 2A) total progenitors (>50 cell colonies; FIG. 2B) were determined per culture flask (y axes). Cell cycle status was assessed by determining the percentage of cells traversing S phase (synthesizing DNA) by treating the cells in vitro with tritiated thymidine ($^3$HtdR) and determining the percentage of cells killed.

DETAILED DESCRIPTION

Figure 1:
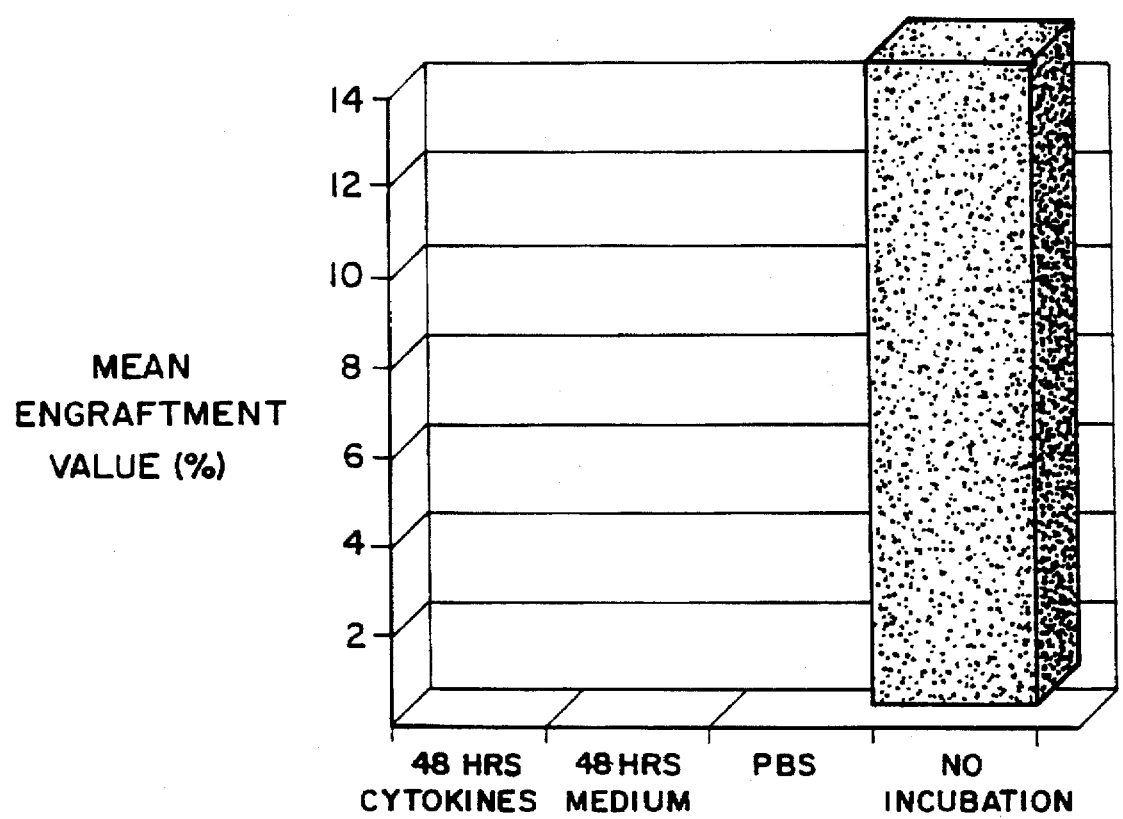
FIG. 1 is a graph of the results of a study on the influence of preincubation of donor bone marrow cells in growth medium containing the cytokines IL-3, IL-6, IL-11, and SCF. Mean engraftment of male donor bone marrow cells into female BALB/c host mice was determined (y axis). For Group 1 host mice, donor cells were incubated for 48 hours in culture medium plus IL-3, IL-6, IL-11, and SCF. Three injections each of $40\times10^6$ cells were given to host mice. For Group 2 host mice, donor cells were incubated for 48 hours in culture medium alone. Three injections each of $40\times10^6$ cells were given to host mice. For Group 3 host mice, three injections each of 0.5 ml PBS (phosphate buffered saline lacking cells) were given to host mice. Donor cells administered to Group 4 mice were not incubated prior to giving three injections each of $40\times10^6$ cells to host mice.

Animals. Male and female BALB/c mice were obtained from the Jackson Laboratory (Bar Harbor, Me.).

EXAMPLE 1

Introduction of quiescent stem cells into a mammal is accomplished by injection into a vein of a mammal (such as a human or a mouse). Injection volumes were the same in each experiment and ranged from 0.5 to 1.0 ml. A portion of the injected stem cells populate the bone marrow, spleen and thymus. The injected stem cells or transfected stem cells can be from the host mammal (autologous transplantation) or the cells can be from a different mammal of the same species (allogenic transplantation).

Engraftment was assessed following the injection of $40\times10^6$ male BALB/c mouse bone marrow stem cells for each of five days into female BALB/c host mice. The percent of male cells or male DNA in host tissue at various times post transplantation was determined by standard cytogenetic techniques (Stewart, F. M. et al. (1993) Blood 81:2566–2571) allowing identification of male cells as those cells lacking heterochromatic staining at the centromere (c-banding). Alternatively, Southern analysis using a labelled (e.g., radiolabelled) Y chromosome-specific DNA probe was used to analyze the percent engraftment of male donor cells into female host bone marrow as defined above. A useful Y chromosome-specific probe is the pY2 cDNA probe (Lamar, E. E. and Palmer, E. (1984) Cell 37:171; or other mouse Y chromosome-specific DNA probe) a probe which hybridizes to repetitive sequences on the murine Y chromosome.

Southern analysis to detect the degree of engraftment of male cells into female bone marrow was performed using standard techniques (see e.g., Sambrook, et al. (1989) Molecular Cloning: A Laboratory Manual. Cold Spring Harbor Laboratory Press). Typically DNA extracts of murine tissue (such as bone marrow) was prepared by lysis in 0.15 mol/L NaCl, 0.02 mol/L Tris, 0.02 mol/L EDTA, 1% sodium dodecyl sulfate (SDS), followed by purification using organic extraction with proteinase K, pancreatic RNAse, and phenol-chloroform followed by precipitation in ethanol. DNA samples were analyzed for the presence of Y chromosome-specific sequences using the pY2 cDNA probe. These samples were digested with the restriction enzymes DraI and BamHI and the digested fragments separated by gel electrophoresis in 0.8% agarose. Equal amounts of digested DNA, as determined by 260/280 ratios, were loaded per gel and the comparability of loaded DNA was determined by reprobing membranes with a partial- or full-length cDNA for interleukin-3 (IL-3) or other marker cDNA. The DNA fragments were transferred from the gel onto Zetaprobe nylon membranes (BioRad, Richmond, Calif.) according to established Southern blotting techniques. The pY2 probe was labeled with $^{32}$p using a random primer labeling kit (Boehringer Mannheim, mannheim, Germany); hybridization with Zetaprobe membranes was performed in 10% dextran sulfate, 1% SDS, 1X Denhardt's, 4X SSCP at 65° C. for 18 to 22 hours. Autoradiography was performed using Kodak XRP x-ray film with or without enhancing screens (Eastman Kodak, Rochester, N.Y.) at −70° C. for varying time intervals. The percentage of male DNA in female host tissue was calculated based on densitometry comparisons between posttransplant DNA samples and male murine DNA. Densitometry was performed on an LKB ultrascan XL enhanced laser densitometer (LKB Pharmacia, Uppsala, Sweden). Calculations of percent DNA were adjusted based on amounts of DNA loaded on each gel as estimated by densitometry of IL-3-probed Southern blots. The detection limit for male DNA in a mixture of male and female DNA was approximately 3% under these conditions.

EXAMPLE 2

Administration of a cell cycle inducing agent adversely affects the capability of the harvested cells to engraft in a non-myeloablated host (Ramshaw, H. S. et al. (1994) Experimental Hematology, 22:823). Bone marrow harvested from BALB/c mice six days after the mice had received 150 mg/kg 5-fluorouracil by tail vein injection was markedly inferior to normal bone marrow. In these studies, two tibia/two femur equivalents (or approximately $40\times10^6$ bone marrow cells) of male marrow where transplanted by tail vein injection on each of five consecutive days into non-myeloablated female hosts. Engraftment was assessed in DNA of host female splenic and thymic tissues by Southern analysis of pY2 hybridizing sequences at 1, 2, 3, 10 and 20 months following the last transplantation. For host mice receiving bone marrow from 5-FU-treated male mice, the mean bone marrow engraftment was 8% at 3 months post transplantation as compared to 38% for host mice receiving bone marrow from untreated male mice. This 5-FU treatment defect was also observed at 3 months post-transplantation in host female splenic and thymic tissues (Stewart et al. (1993) Blood 81:2566–2571)

The engraftment defect seen after 5-FU treatment is a transient functional defect and appears to be due to the induction of quiescent stem cells into active cell cycling (Ramshaw, H. S. et al. (1994) Experimental Hematology, 22:823). Bone marrow cells from 5-FU-treated male mice six days after treatment were found by hydroxyurea suicide analysis to be in active cell cycle. In contrast, bone marrow cells harvested from 5-FU-treated male mice 35 days after treatment or from untreated male mice were not in active cell cycle and exhibited engraftment capabilities superior to those of 5-FU-treated cells (see Table 1).

TABLE 1

| | % Engraftment | |
|---|---|---|
| | Bone-marrow | Spleen |
| Control donor marrow | 38.1 | 33.1 |
| Day 6 post 5-FU | 18.1 | 16.5 |
| Day 35 post 5-FU | 35.3 | 32.9 |

% Engraftment values were determined by densitometry of Southern blots (not corrected for loading on the gel) on 4 or 5 mice per group.

EXAMPLE 3

Cytokine incubation of murine bone marrow cells impairs the capacity to repopulate in non-myeloablated hosts. Incubation of murine or human hematopoietic cells with various cytokine combinations has been used to expand stem cell populations and induce stem cell replication resulting in enhanced gene-carrying retroviral integration. This study examined the effect of a 48 hour in vitro incubation in cell culture medium (DMEM-Low glucose, 15% fetal calf serum) with a cytokine combination of murine IL-3-CHO (50 U/ml), murine IL-6 (50 U/ml), murine IL-11 (50 ng/ml), and murine SCF (50 U/ml) on engraftment of male donor bone marrow cells into non-myeloablated female BALB/c host mice. A second group of donor cells was incubated with medium alone and a third group of donor cells was not incubated. In each group three injections of $40 \times 10^6$ cells per injection were made over three days. Engraftment was evaluated by Southern analysis using a Y chromosome-specific probe (pY2). Neither the cytokine-incubation group, nor the medium-only incubation group demonstrated evidence of male DNA sequence, indicating that no engraftment occurred. The control group which received cells immediately after donor collection, showed a 16.6% engraftment level (range 11.6–24.8%, n=4) in host bone marrow. This result is consistent with the previous observation that pre-treatment with a cell cycle inducing agent, 5-FU, causes decreased engraftment (Stewart et al. (1993), supra) and indicates that exposure to cytokines and/or inducement of active cell cycling impairs engraftment and repopulating capacity of hematopoietic stem/progenitor cells in non-myeloablated hosts.

EXAMPLE 4

Cytokines are used for the in vitro expansion of hematopoietic progenitor/stem cells resulting in an increased percentage of stem cells in active cell cycling. An evaluation of the level of engraftment as a function of the cell cycle in which the population of donor cells reside was performed.

Figure 2A:
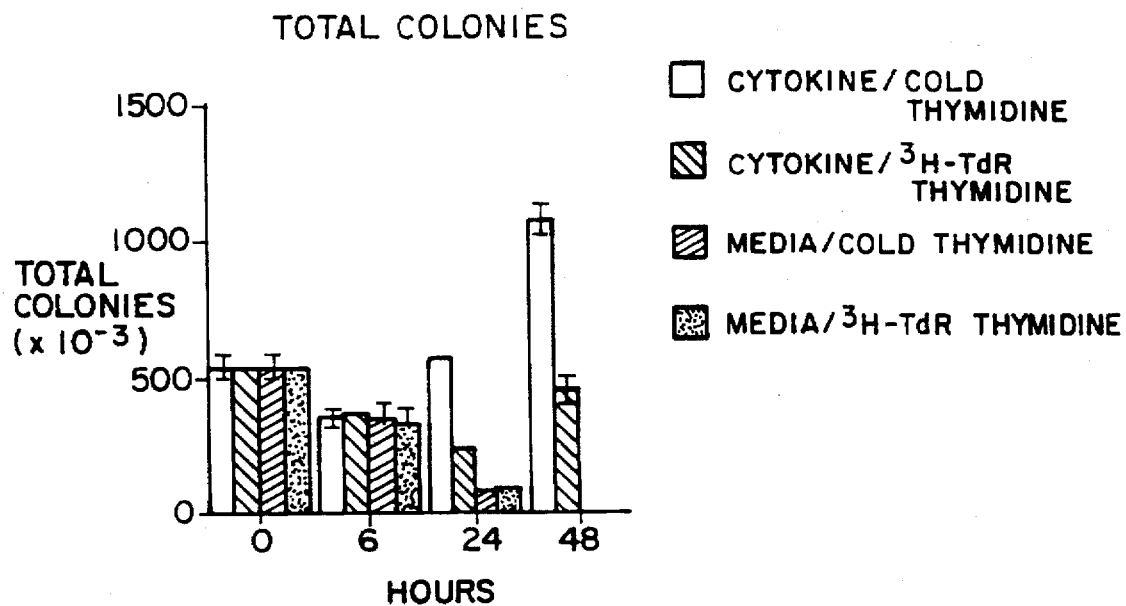
FIGS. 2A and 2B are bar graphs showing the results of studies in which male BALB/c mouse bone marrow was incubated in culture media alone or in media plus IL-3 (50 U/ml), IL-6 (50 U/ml), IL-11 (50 ng/ml), and steel factor (c-Kit ligand, 50 U/ml; Genetics Institute, Cambridge, Mass.) for 6, 24, or 48 hours (x axes). High proliferative potential colony-forming cells (HPP-CFC.
Figure 2B:
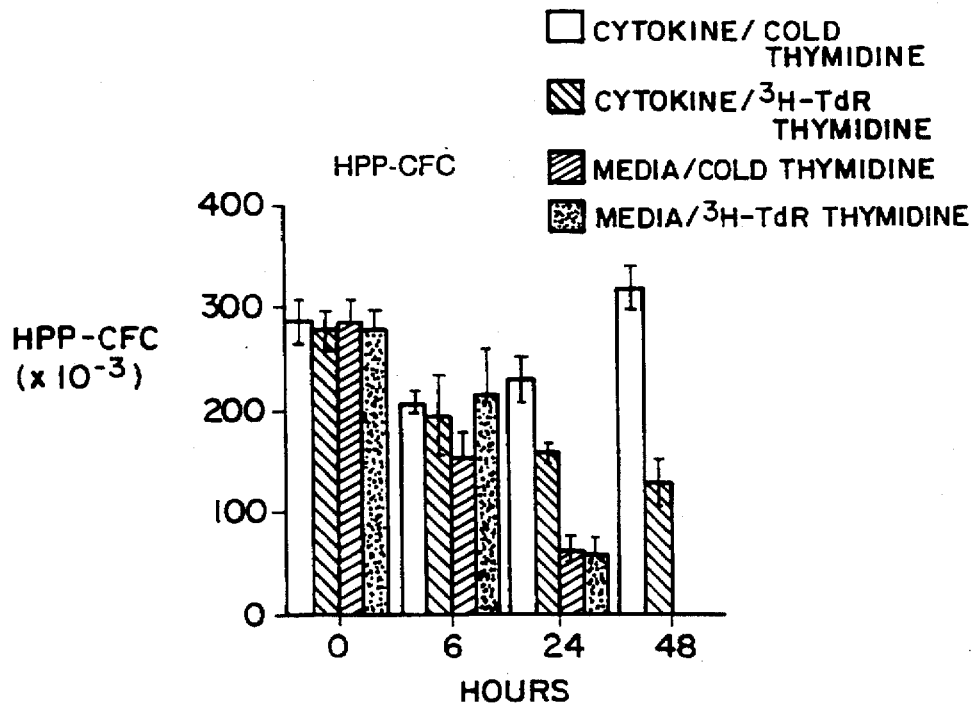

Male BALB/c donor bone marrow cells were exposed in vitro to IL-11 (50 ng/ml), IL-6 (50 U/ml), IL-3 (50 U/ml), and steel factor (c-Kit ligand, 50 U/ml) for 48 hours. This combination of cytokines has been used to enhance retroviral integration in vitro in primitive progenitor/stem cells. Control donor cells were exposed to culture media without cytokines for 48 hours. The proportion of the cells in active cell cycling was measured by the percentage of cells killed by 20 minute exposure to high specific activity tritiated thymidine ($^3$HtdR) (FIG. 2A). Donor cells were also evaluated for the effects of in vitro liquid culture on HPP-CFC (multi-factor responsive) and total progenitors (FIGS. 2A and 2B). At initiation of the cultures there was less than 3.5% killing in both the cytokine-exposed and media-only cell cultures indicating that the donor cells were in the quiescent ($G_1$ or $G_0$) phase. There was a progressive increase in killing at 6, 24, and 48 hours (FIGS. 2A and 2B) in the cytokine-treated cell cultures. Donor bone marrow cells incubated in vitro with cytokines show a maintenance of multi-factor responsive HPP-CFC (111% of input) and an expansion of total progenitors (199% of input) with a concomitant progression from quiescence to active cell cycling. Initial $^3$HtdR killing was 3.5% and 1.0% of HPP-CFC and total progenitor, respectively. After 48 hours the proportions of cells killed by exposure to $^3$HtdR were 60% and 58%, respectively (FIGS. 2A and 2B).

Four groups of male mouse donor bone marrow cells were evaluated for engraftment into normal non-myeloablated BALB/c female mice. Staggered liquid marrow cultures were established and female BALB/c non-myeloablated hosts were transplanted with $40 \times 10^6$ non-cultured male BALB/c bone marrow cells for three consecutive days (total of $120 \times 10^6$ cells) or the equivalent of $40 \times 10^6$ cultured cells exposed or not exposed to the cytokine regimen described above. Engraftment at 35 days following the last transplantation was evaluated by Southern blot analysis using the pY2 probe or by FISH analysis (Fluorescence In Situ Hybridization analysis, a standard technique well known to those of ordinary skill in the relevant arts) (FIG. 1). Non-cultured donor bone marrow cells showed a mean engraftment of approximately 15% while no engraftment was observed with cells cultured in media alone or media with cytokines (IL-3, IL-11, IL-6, and steel factor).

EXAMPLE 5

Exposure of donor bone marrow cells to cytokines is useful to enhance retroviral integration for the formation of transfected cells. Engraftment of transfected cells was examined to evaluate the usefulness of such cells in a gene therapy regimen.

Male BALB/c bone marrow cells were transfected with a retroviral vector carrying the MDR gene to produce transfected cells. The transfection protocol involved inducing the cells into cell cycle by cytokine exposure and provided over 90% MDR transfection into the primitive stem cells (HPP-CFC). The transfected cells were transplanted into female BALB/c mice on 5 consecutive days (one transplantation per day for a total of $45 \times 10^6$ cells transplanted over 5 days). Following the last transplantation, the mice were treated three times with Taxol (10 mg/kg IP) over 7 months to expand the MDR-carrying stem cells in vivo. At 14 months following transplantation, the recipient mice were sacrificed for analysis of engraftment and the presence of the MDR gene. There was a 8.9%–13.4% engraftment of male transfected cells into female hosts as determined by Southern analysis using the pY2 probe. However, there was only minimal expression in 3 of 4 transplanted animals of the MDR gene as determined by RT-PCR (reverse transcriptase-polymerase chain reaction). Thus, cycling murine stem cells successfully integrated the MDR gene following retroviral infection in vitro but very few of the cells which engrafted were carrying the gene. This suggests that dormant $G_0$ cells without the retroviral gene construct were able to engraft and that a critical feature of successful engraftment is the use of dormant cells. Effective gene transfer requires that the stem cells be returned to a quiescent state prior to transplantation.

EXAMPLE 6

Preparation of quiescent stem cells for transplantation is accomplished by multiple techniques. In a first method, noncycling stem cells are isolated from a mammal which has not been treated with a cell cycle inducing agent for a period of time sufficient to allow at least 50%, preferably at least 70%, most preferably at least 80% of the stem cells to return to the quiescent $G_1$ or $G_0$ phase of the cell cycle. Such quiescent bone marrow stem cells are used directly for transplantation into a non-myeloablated mammal.

Actively cycling stem cells can be isolated from a mammal treated with a cell cycling inducing agent or the harvested stem cells can be treated in vitro with a cell proliferation agent (e.g., a cytokine) to increase the number of stem cells or to enhance in vitro retroviral infection for use in ex vivo gene therapy. Subsequently, actively cycling stem cells are induced to become quiescent by removing nutrients from the culture medium (e.g., serum starvation) causing at least 50%, preferably at least 70%, more preferably at least 80% of the cells to enter the $G_0$ cell cycle phase. The quiescent stem cell population is then transplanted into a host mammal.

Use

Diseases that are treated by transplantation of bone marrow stem cells and for which treatment can be enhanced by the method of the invention include, but are not limited to, diseases such as lymphoma, multiple myeloma, breast cancer, testicular cancer, leukemias, congenial hemolyticanemias (sickle cell anemia and thalassaemia) and some immunodeficiency diseases (e.g., acute leukemia, Hodgkin's and non-Hodgkin's lymphoma, and neuroblastoma).

Several human diseases may be treated by ex vivo gene therapy involving transplantation of transfected bone marrow stem cells and such treatment can be enhanced by the method of the invention. Correction of human inherited disorders in bone marrow stem cells in tissue culture has been shown for Gaucher disease in which the mutant glucocerebrosidase-encoding gene is replaced by the wild type gene. Dihydrofolate reductase deficiency in which a mutated from of the dihydrofolate reductase-encoding gene (DHFR) is replaced has been performed in mice (Watson, J. D. et al., Recombinant DNA, 2nd ed., pp. 571–576).

Ex vivo gene therapy in large animals such as humans presents several difficulties that can be alleviated by enhancement of stem cell engraftment following transplantation of quiescent cells. In one set of studies using macaque monkeys, bone marrow cells from the monkeys were infected with a vector carrying a human cDNA for adenosine deaminase. The donor monkeys received total body irradiation and then an infusion of infected cells. Only low levels of expression of human adenosine deaminase-encoding cDNA could be detected in these mammals. Similar results were obtained in experiments with bone marrow cells that carried the human β-globin gene (Watson, J. D. et al., Recombinant DNA, 2nd ed., pp. 571–576). Such reduced expression can be enhanced by the method of the invention in which quiescent transfected stem cells are transplanted into the non-myeloablated recipient mammal. Finally, transfer of a normal human adenosine deaminase gene (ADA) into a human patient for the treatment of severe combined immune deficiency caused by a mutation in ADA has been achieved with encouraging results using bone marrow-stem cell gene therapy in humans (Watson et al. (1992), Supra, p. 578). However, the treatment required that the patients receive gene-corrected cells every 1 to 2 months for up to one year before showing signs of clinical improvement. The instant invention is useful in enhancing the engraftment at each treatment and thereby more quickly and assuredly improve the health of the patient.

What is claimed is:

1. A method of introducing cells into a host mammal, said method comprising the steps of:
    a) providing a population of pluripotent hematopoietic stem cells;
    b) expanding said population of stem cells to yield a population of expanded stem cells;
    c) treating said population of expanded stem cells to induce said population of expanded stem cells to become quiescent stem cells; and
    d) introducing said quiescent stem cells into said host mammal.

2. A method of introducing transfected cells into a host mammal, said method comprising the steps of:
    a) providing a population of transfected pluripotent hematopoietic stem cells;
    b) inducing said population of transfected stem cells to become quiescent transfected stem cells; and
    c) introducing said quiescent transfected stem cells into said host mammal.

3. The method of claim 1, wherein said introducing step comprises the steps of:
    i) introducing a fraction of said quiescent stem cells into said host at a first point in time; and
    ii) introducing after the first point in time additional fractions of said quiescent transfected stem cells in at least five and not greater than fifteen additional administrations, each spaced from the other by at least 12 hours.

4. The method of claim 2, wherein said introducing step comprises the steps of:
    i) introducing a fraction of said quiescent transfected stem cells into said host at a first point in time; and
    ii) introducing after the first point in time additional fractions of said quiescent transfected stem cells in at least five and not greater than fifteen additional administrations, each spaced from the other by at least 12 hours.

5. The method of claim 1 or claim 2, wherein said cells are selected from the group consisting of allogenic bone marrow cells, autologous bone marrow cells, peripheral-blood cells, and cord blood stem cells.

6. A method of claim 1 or 2, wherein said host mammal is non-myeloablated.

* * * * *